(12) United States Patent
Bourdon et al.

(10) Patent No.: US 12,257,164 B2
(45) Date of Patent: Mar. 25, 2025

(54) IMPLANT DEVICE

(71) Applicant: Statera Medical Inc., Montreal (CA)

(72) Inventors: Samuel Bourdon, Montreal (CA); Frédérik Plourde, Montreal (CA)

(73) Assignee: Statera Medical Inc. (CA)

( * ) Notice: Subject to any disclaimer, the term of this patent is extended or adjusted under 35 U.S.C. 154(b) by 243 days.

(21) Appl. No.: 17/881,977

(22) Filed: Aug. 5, 2022

(65) Prior Publication Data

US 2024/0041617 A1 Feb. 8, 2024

(51) Int. Cl.
| | |
|---|---|
| A61F 2/30 | (2006.01) |
| A61F 2/32 | (2006.01) |
| A61F 2/34 | (2006.01) |
| A61F 2/40 | (2006.01) |
| A61F 2/46 | (2006.01) |
| A61F 2/36 | (2006.01) |

(52) U.S. Cl.
CPC ............ *A61F 2/4657* (2013.01); *A61F 2/30* (2013.01); *A61F 2/30734* (2013.01); *A61F 2/32* (2013.01); *A61F 2/34* (2013.01); *A61F 2/40* (2013.01); A61F 2002/30156 (2013.01); A61F 2002/30405 (2013.01); A61F 2002/30654 (2013.01); A61F 2002/3611 (2013.01); A61F 2002/4022 (2013.01); A61F 2002/4085 (2013.01); A61F 2002/4666 (2013.01); A61F 2002/469 (2013.01)

(58) Field of Classification Search
CPC .... A61F 2/30; A61F 2/581; A61F 2/32; A61F 2002/30649; A61F 2/4081; A61F 2/34; A61F 2002/3208; A61F 2002/5096; A61F 2002/4666; A61F 2/40; A61F 2002/30565; A61F 2/4657; A61F 2/30734; A61F 2002/30654; A61F 2002/3611; A61F 2002/4022; A61F 2002/4085; A61F 2002/469; A61F 2002/30405; A61F 2002/30156
See application file for complete search history.

(56) References Cited

U.S. PATENT DOCUMENTS

| | | | |
|---|---|---|---|
| 2009/0087253 A1 | 4/2009 | Spratte et al. | |
| 2012/0209394 A1* | 8/2012 | Bojarski | A61F 2/4202 623/18.11 |
| 2017/0065433 A1* | 3/2017 | Singh | A61F 2/32 |
| 2020/0107945 A1* | 4/2020 | Trousdale | A61B 5/0031 |

* cited by examiner

*Primary Examiner* — Dinah Baria
(74) *Attorney, Agent, or Firm* — Foley & Lardner LLP

(57) ABSTRACT

Systems and methods to evaluate a joint implant device are provided. The joint implant device can include a socket that at least partially receives a first joint component. The joint implant device can include a socket housing coupled with the socket. The joint implant device can include a first sensor, a second sensor, and a third sensor each disposed between the socket and the socket housing. The joint implant device can include a socket extension coupled with the socket. The joint implant device can include a socket housing extension coupled with the socket housing. The joint implant device can include a fourth sensor disposed between the socket extension and the socket housing extension. At least three of the first sensor, the second sensor, the third sensor, or the fourth sensor can detect a force between the socket and the first joint component.

20 Claims, 15 Drawing Sheets

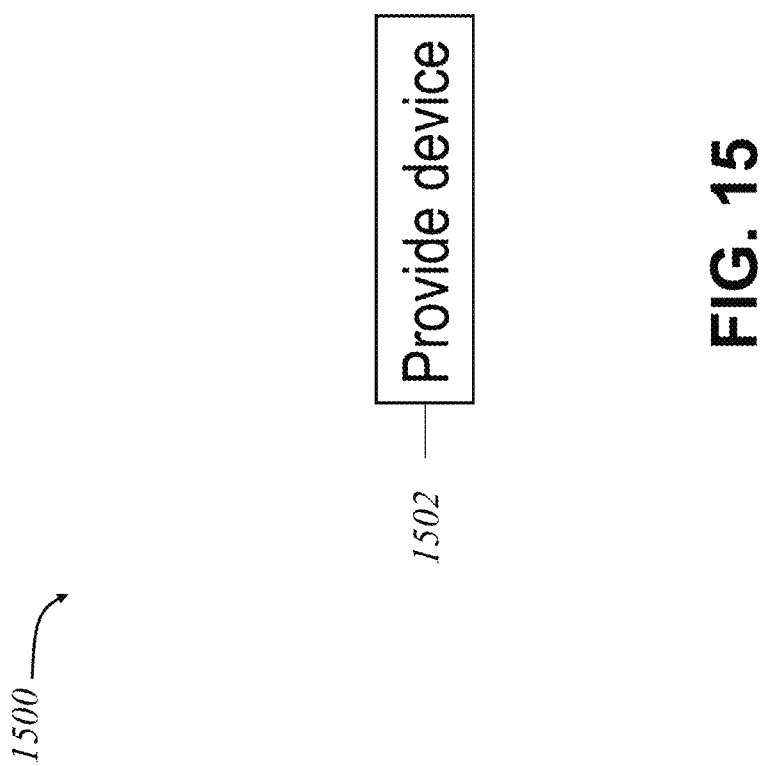

IMPLANT DEVICE

BACKGROUND

Various medical devices can be used to support several bones, muscles, ligaments, or tendons in a body.

SUMMARY

At least one aspect is directed to a joint implant device. The joint implant device can include a socket that at least partially receives a first joint component. The joint implant device can include a socket housing coupled with the socket. The joint implant device can include a first sensor, a second sensor, and a third sensor each disposed between the socket and the socket housing. The joint implant device can include a socket extension coupled with the socket. The joint implant device can include a socket housing extension coupled with the socket housing. The joint implant device can include a fourth sensor disposed between the socket extension and the socket housing extension. At least three of the first sensor, the second sensor, the third sensor, or the fourth sensor can detect a force between the socket and the first joint component.

At least one aspect is directed to a method. The method can include providing a joint implant device. The joint implant device can include a socket that at least partially receives a first joint component. The joint implant device can include a socket housing coupled with the socket. The joint implant device can include a first sensor, a second sensor, and a third sensor each disposed between the socket and the socket housing. The joint implant device can include a socket extension coupled with the socket. The joint implant device can include a socket housing extension coupled with the socket housing. The joint implant device can include a fourth sensor disposed between the socket extension and the socket housing extension.

At least one aspect is directed to a method of providing a joint implant device. The method can include at least partially receiving, by a socket, a first joint component. The method can include coupling a socket housing with the socket. The method can include disposing a first sensor, a second sensor, and a third sensor between the socket and the socket housing. The method can include coupling a socket extension with the socket. The method can include coupling a socket housing extension with the socket housing. The method can include disposing a fourth sensor between the socket extension and the socket housing extension. The method can include detecting, by at least three of the first sensor, the second sensor, the third sensor, or the fourth sensor, a force between the socket and the first joint component.

At least one aspect is directed to a method. The method can include providing a joint implant device. The joint implant device can include a socket that at least partially receives a first joint component. The joint implant device can include a socket housing coupled with the socket. The joint implant device can include a first sensor, a second sensor, and a third sensor each disposed between the socket and the socket housing. The joint implant device can include a socket extension coupled with the socket. The joint implant device can include a socket housing extension coupled with the socket housing. The joint implant device can include a fourth sensor disposed between the socket extension and the socket housing extension. The method can include detecting, by at least three of the first sensor, the second sensor, the third sensor, or the fourth sensor, a force between the socket and the first joint component.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings:

FIG. 15 is an example illustration of a method, in accordance with implementations.

DETAILED DESCRIPTION

Figure 1:
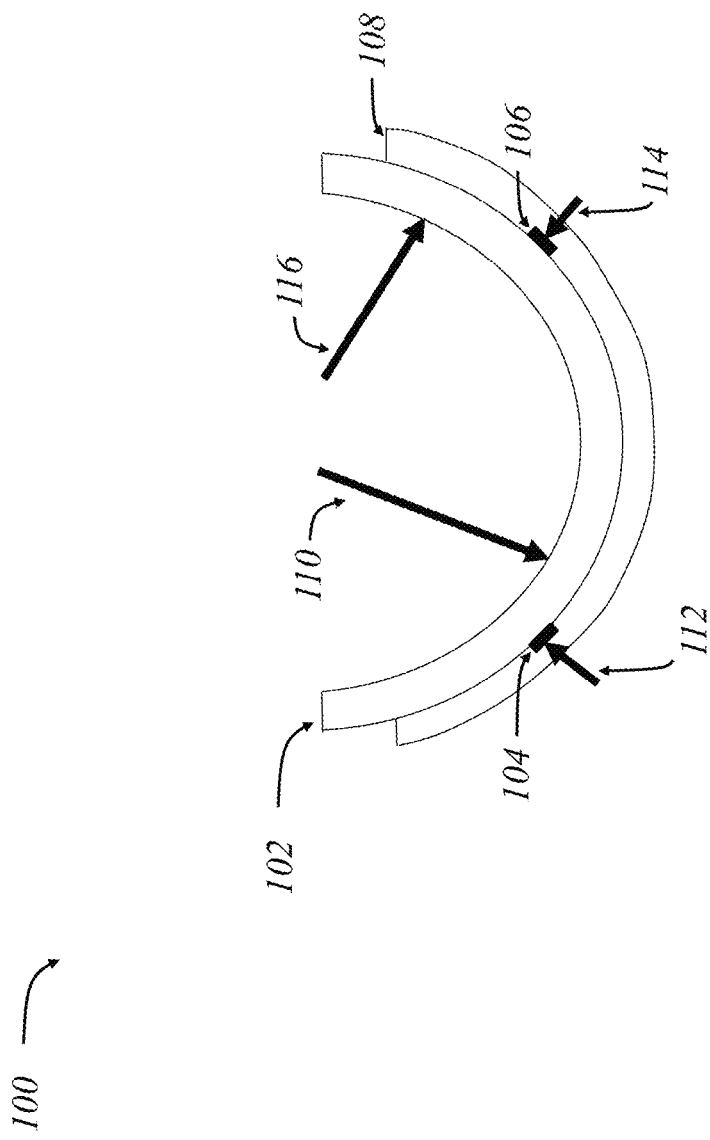
FIG. 1 is an example side schematic view of a joint implant device, in accordance with implementations.

Following below are more detailed descriptions of various concepts related to, and implementations of, methods, apparatuses, and systems of medical devices. The various concepts introduced above and discussed in greater detail below may be implemented in any of numerous ways.

The present disclosure generally relates to systems and methods for providing and evaluating a joint implant device. The joint implant device can be used in joint replacement operations to support or replace joints. The technical solution is generally directed to a medical device. For example, this technical solution is generally directed to a joint implant device for coupling to a joint of a human body such as a knee joint, shoulder joint, hip joint, ankle joint, or elbow joint. Generally, joints of a human body, such as the shoulder joint, are complex in nature. During joint replacement or reparation surgery, restoring the center of rotation may include evaluating soft tissue tension and balance about the joint, as soft tissues play an important role in optimizing joint function for joint replacement surgery.

Current joint replacement implants focus on bone anatomy and alignment without addressing soft tissue tension. However, optimizing soft tissue tension would provide several advantages. Conventional implants include a fixed inclination and rely on subjective measures to cut bones to achieve the desired height, tilt, inclination, or rotation of the implant. Thus, achieving adequate soft tissue tension is difficult and there is a need to detect tension or compression loads at the joint.

This is a particularly important with shoulder implants for shoulder dislocation or any joint implant device that generally has a ball and socket joint form, as it is very difficult to detect magnitude and direction of a load force of an unconstrained or semi-constrained ball and socket joint.

This technical solution provides a prosthesis with sensors to provide surgeons with objective data regarding an orientation, location, and amplitude of force on the prosthesis. Furthermore, this technical solution provides an accurate force magnitude and direction reading using compression sensors along an entire interface between a ball and socket joint of the prosthesis.

Further, this technical solution may have many benefits over existing medical device evaluating systems. For example, by determining accurate and objective data measurements using various computing devices and sensors over an interface of a joint, the technical solution may provide more precise physical metrics of a medical device in comparison to manual evaluation techniques. Furthermore, since typically known evaluation and adjustment techniques are generated manually, such adjustments are often derived based on subjective data on a case-by-case and practitioner-by practitioner basis. This technical solution provides for real-time, repeatable, and accurate evaluation outcomes to more efficiently and effectively adjust a medical device to meet patient needs. Various other technical benefits and advantages are described in greater detail herein.

The present disclosure generally relates to a joint implant device that includes a ball and socket joint. The joint implant device can include a plurality of sensors to detect a magnitude and direction along an interface between the ball and socket of the ball and socket joint. For example, the joint implant device can include at least three sensors equally spaced in a circumferential direction about the socket. The joint implant device can include at least one sensor coupled with extensions of the joint implant device to facilitate determining magnitude and direction of a force between the ball and socket if the force falls out of a range of the equally spaced sensors. For example, the present disclosure is directed towards extending the surfaces of the socket and a socket housing such that a reaction load force may be induced between the extended surfaces over the entire range of input force positions. One or more sensors may be placed at contact point(s) between the extended surfaces.

Figure 2:
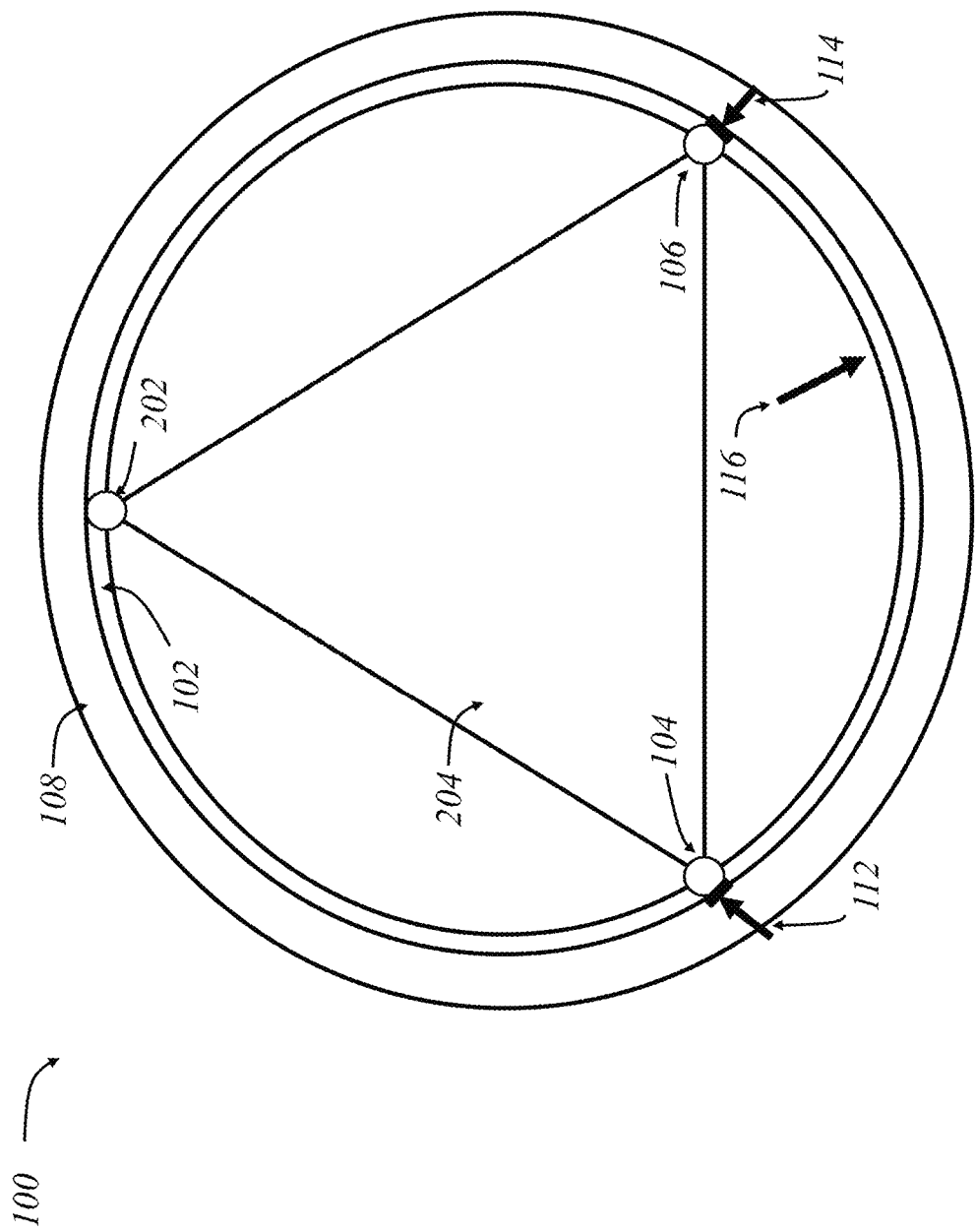
FIG. 2 is an example top schematic view of the joint implant device of FIG. 1, in accordance with implementations

FIG. 1 depicts an example side view schematic of a joint implant device 100. For example, FIG. 1 depicts a 2D schematic of the implant device 100. FIG. 2 depicts an example top view schematic of the implant device 100. The implant device 100 can be or can include a ball and socket joint. For example, the implant device 100 can be or can include a prosthesis body for coupling with a portion of a joint (e.g., a shoulder joint, hip joint, knee joint, elbow joint, or other joint). The implant device 100 can include a socket 102 and a socket housing 108. The socket 102 can include one or more surfaces or openings that can receive a ball 402 (visible in at least FIG. 4). The socket housing 108 can be or can include one or more surfaces, areas, or structures that can support the socket 102 (e.g., contact, surround, engage, abut, or position beneath the socket 102).

The implant device 100 can couple with various joints in a body such as a shoulder joint, a hip joint, an ankle joint, a knee joint, a wrist joint, an elbow joint, or another joint. While the joint implant device 100 described in reference to the figures generally describes a shoulder or hip joint (e.g., a ball and socket joint), the joint implant device 100 can be used with various other joints. The implant device 100 can include one or more prosthesis bodies, for example. The implant device 100 can be made from various components and materials including, but not limited to, non-metallic materials (plastic, rubber, or another materials) or metallic materials (e.g., aluminum, steel, titanium, or another material).

The socket 102 can include one or more sensors. For example, the socket 102 can include a first sensor 104, a second sensor 106, a third sensor 202 (visible in at least FIG. 2), or more sensors. The sensors can be disposed along an interface between the socket 102 and the socket housing 108 (e.g., such that the sensors are embedded between the socket 102 and the socket housing 108). The sensors can facilitate detecting a physical parameter of the implant device, such as a load force of the implant device 100 or various other parameters (e.g., pressure, stability). For example, the sensors can facilitate detecting a magnitude and direction of a force applied on a portion of the implant device 100 (e.g., a force of the ball 402 applied on the socket 102 or a force of the socket 102 applied on the ball 402 or various other forces). At least one of the first sensor 104, the second sensor 106, or the third sensor 202 can include or can be a compression sensor. The sensors can be or can include various other sensors including, but not limited to, resistive sensors. For example, the sensors can detect or measure a temperature, pressure, displacement, force, vibration, or the like occurring on or about a surface of the socket 102 (e.g., an annular surface that receives or contacts the ball 402). The sensors can detect a physical metric of the implant device 100 based on a change in voltage or resistance of the sensors. For example, the sensors can be or can include an accelerometer, gyroscope, geomagnetic sensor, potentiometer, transducer, thermistor, strain gauge, or the like.

The sensors can be substantially (e.g., within 10%) equally distributed about the socket 102, the ball 402, or the socket housing 108. For example, as depicted in at least FIG. 2, the first sensor 104, the second sensor 106, and the third sensor 202 can be disposed equally in a circumferential direction about a center portion of the socket 102 such that the spacing of the sensors forms a triangular area 204 (e.g., an equilateral triangle formed between center points of the sensors). The area 204 can vary in shape and position depending on the shape, size, and positioning of the sensors. The spacing of the first sensor 104, the second sensor 106, and the third sensor 202 can allow for a reading of magnitude and direction of a load force applied anywhere within the triangular area 204. For example, as depicted in at least FIG. 1, a first load force 110 can be applied within the triangular area 204 (e.g., applied in the region that lies between the first sensor 104, the second sensor 106, and the third sensor 202). The first sensor 104 can be compressed by a first reaction load force 112, the second sensor 106 can be compressed by a second reaction load force 114, and the third sensor 202 can be compressed by a third reaction load force (not visible in FIG. 1). These compression forces can generate signals that can be measured and used to reconstruct (e.g., determine the magnitude and direction of) the first load force 110.

As depicted in at least FIGS. 1 and 2, a second load force 116 can be applied outside of the region covered by the sensors (e.g., outside the triangular area 204). In this circumstance, there may be no compression induced in at least one of the sensors (e.g., the third sensor 202), and the second load force 116 may no longer be accurately reconstructed without an additional sensor reading. These load forces are for illustrative purposes. Load forces applied to the implant device 100 can vary in magnitude or direction (e.g., throughout the entire rotation of the ball 402 relative to the socket 102).

Figure 3:
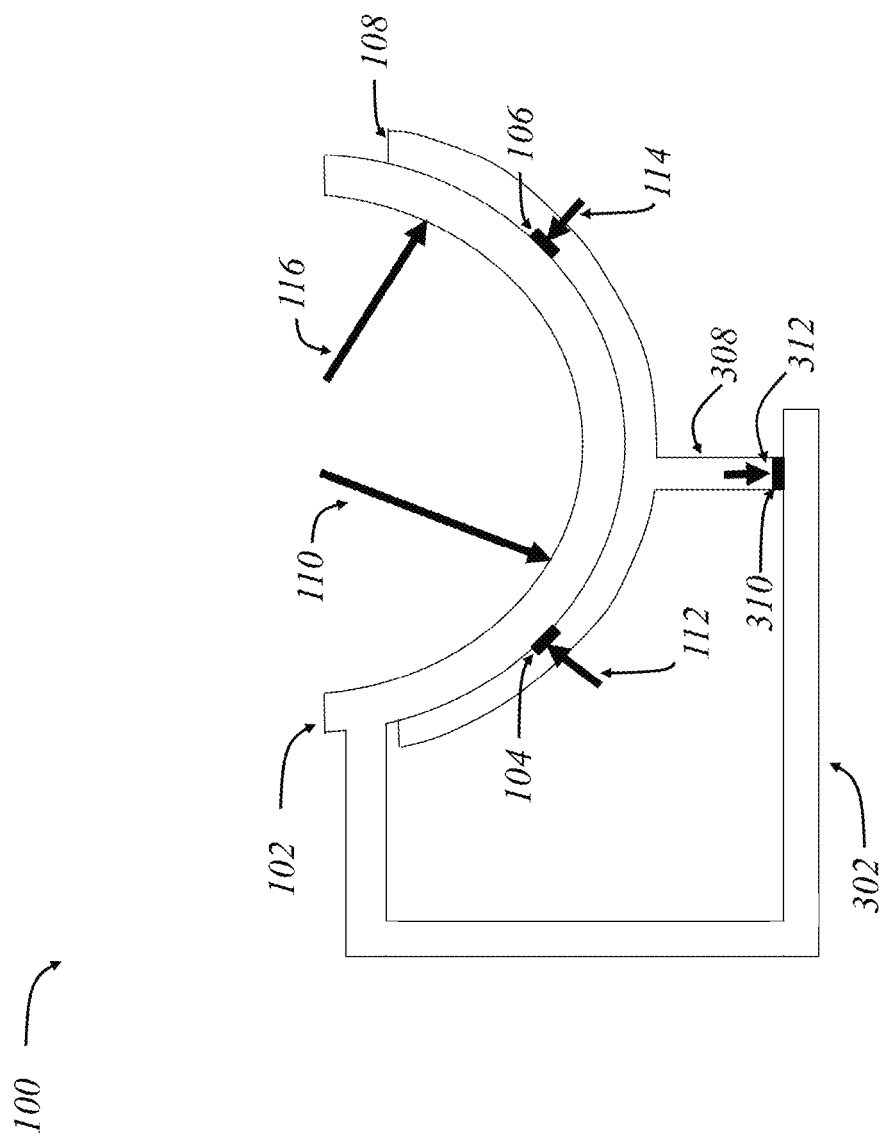
FIG. 3 is an example side schematic view of a joint implant device, in accordance with implementations.

FIG. 3 depicts a side view of a schematic of the joint implant device 100. The implant device 100 can include a socket extension 302 and a socket housing extension 308. The socket extension 302 or the socket housing extension 308 can be or can include one or more materials coupled with the socket 102 or the socket housing 108. The socket extension 302 or the socket housing extension 308 can be or can include one or more protrusions, extensions, or other features coupled (e.g., rigidly coupled, fixed) with the socket 102 or the socket housing 108.

The implant device 100 can include at least one fourth sensor 310. The fourth sensor 310 can be disposed between the socket extension 302 and the socket housing extension 308. As depicted in at least FIG. 3, the socket extension 302 can be disposed relative to the socket housing extension 308 such that at least one of the first sensor 104, the second sensor 106, or the third sensor 202, or another portion of the implant device 100, can act as a pivot point for the socket 102 relative to the socket housing 108. For example, in a 2D schematic, the second load force 116 is above the second sensor 106 and out of the range of the first sensor 104 (e.g., outside of the area 204). For example, the second load force 116 can cause the socket 102 to pivot slightly about the second sensor 106 in a direction away from the first sensor 104, which can cause the first sensor 104 to lose contact or force of the socket 102 and therefore not obtain an accurate load reading (e.g., no compression force or not enough compression force is applied at the first sensor 104). The pivoting of the socket 102 can cause the socket extension 302 to compress the socket housing extension 308, which can cause a reaction load force 312 to occur at an interface between the socket extension 302 and the socket housing extension 308 (e.g., by creating a lever effect). The reaction load force 312 can cause compression to occur at the fourth sensor 310. In this circumstance, even though the first sensor 104 may not be capable of obtaining an accurate load value, the signal generated from the fourth sensor 310 can supplement or replace the signal from the first sensor 104 to obtain an accurate magnitude and direction of the second load force 116. The fourth sensor 310 can include or can be a compression sensor.

The first sensor 104, the second sensor 106, and the third sensor 202 can be direct sensors since they each can measure a reaction load force directly between the socket 102 and the socket housing 108. The fourth sensor 310 can be an indirect sensor since it can measure a reaction load force between the socket extension 302 and the socket housing extension 308 (e.g., measure the force applied on the socket 102 without directly contacting the socket 102 or without directly receiving the force applied on the socket 102).

Figure 4:
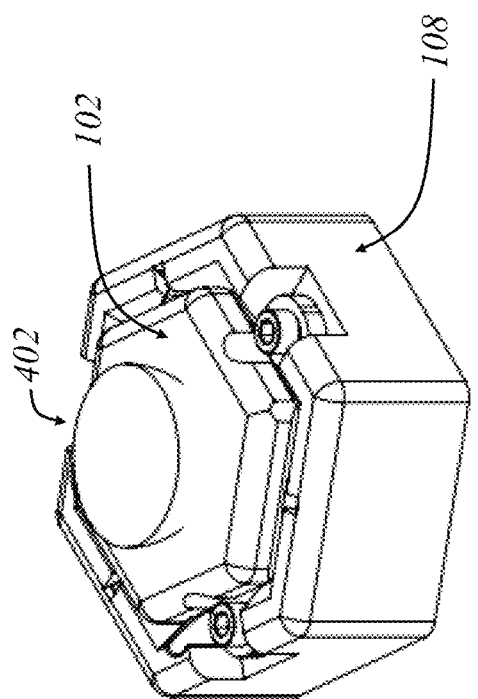
FIG. 4 is an example perspective view of a joint implant device, in accordance with implementations.

FIG. 4 depicts a 3D perspective view of the implant device 100. As described herein, the implant device 100 can include the ball 402, the socket 102 and the socket housing 108. As described herein, the implant device 100 can be used in or coupled with a portion of a joint in a body. For example, in the circumstance of a shoulder joint (e.g., shoulder replacement), the ball 402 can be, can include, can couple with, or can be represented by a glenoid sphere or glenosphere. The socket 102 can be, can include, can couple with, or can be represented by a cup to receive the glenoid sphere. The glenoid sphere can include one or more components to couple with a portion of a shoulder. The socket housing 108 can be, can include, or can be represented by a portion of a body that surrounds or houses the socket 102 and can couple with a humeral component. The ball 402, the socket 102, and the socket housing 108 can be or can couple with various components of other joints including, but not limited to, a tibia component, a femoral component (e.g., a femoral head), a pelvic component, or another portion of the body (e.g., for a hip replacement, knee replacement, elbow replacement, or another procedure for another joint).

Figure 5:
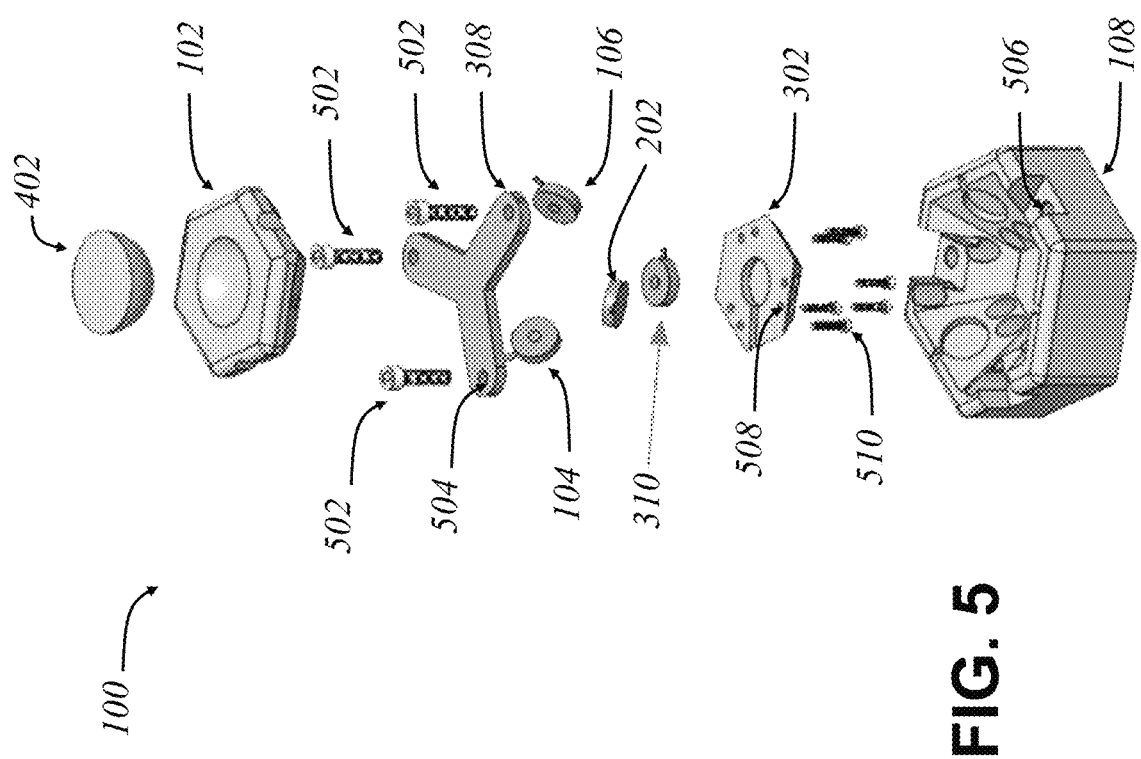
FIG. 5 is an example exploded view of the joint implant device of FIG. 4, in accordance with implementations.

FIG. 5 depicts an example exploded view of the implant device 100. As depicted in FIG. 5, and among others, the implant device 100 can include at least one first fastener 502 that can facilitate coupling the socket housing extension 308 with the socket housing 108. For example, the socket housing extension 308 can include an aperture 504 and the socket housing 108 can include at least one corresponding aperture 506 (e.g., hole, pocket, or another feature) that can align (e.g., overlap) one another to sequentially receive the first fastener 502. For example, the first fastener 502 can penetrate through the aperture 504 of the socket housing extension 308 and the socket housing extension 308 can align with the socket housing 108 such that the first fastener 502 can penetrate through the aperture 506 of the socket housing 108 to rigidly couple the socket housing extension 308 with the socket housing 108.

The implant device 100 can include at least one second fastener 510. The second fastener 510 can facilitate coupling the socket extension 302 with the socket 102. For example, the socket extension 302 can include at least one aperture 508 and an underside portion of the socket 102 can include at least one corresponding aperture 702 (visible in at least FIG. 7) such that the second fastener 510 can penetrate through the aperture 508 of the socket extension 302 and through a portion of the aperture of the socket 102 to couple the socket extension 302 with the socket 102.

Figure 6:
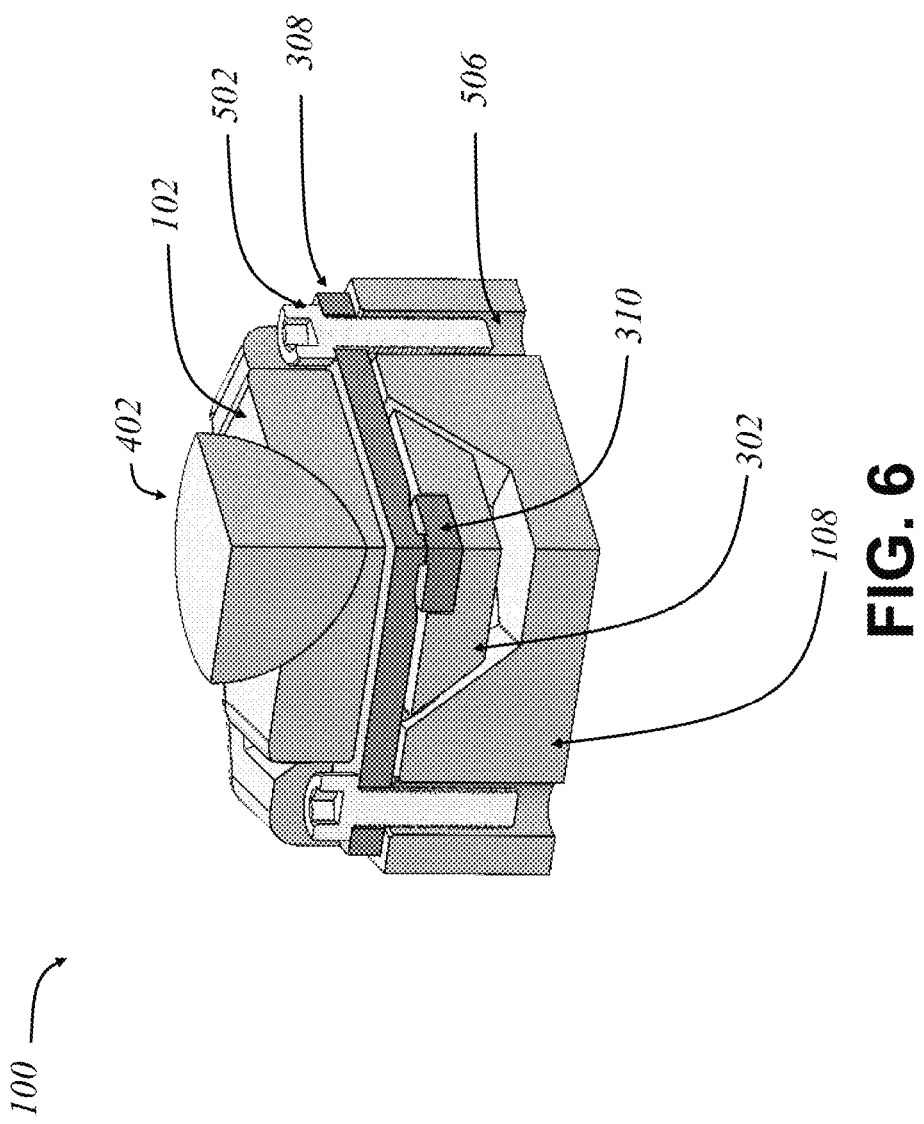
FIG. 6 is an example cross-sectional view of the joint implant device of FIG. 4, in accordance with implementations.
Figure 7:
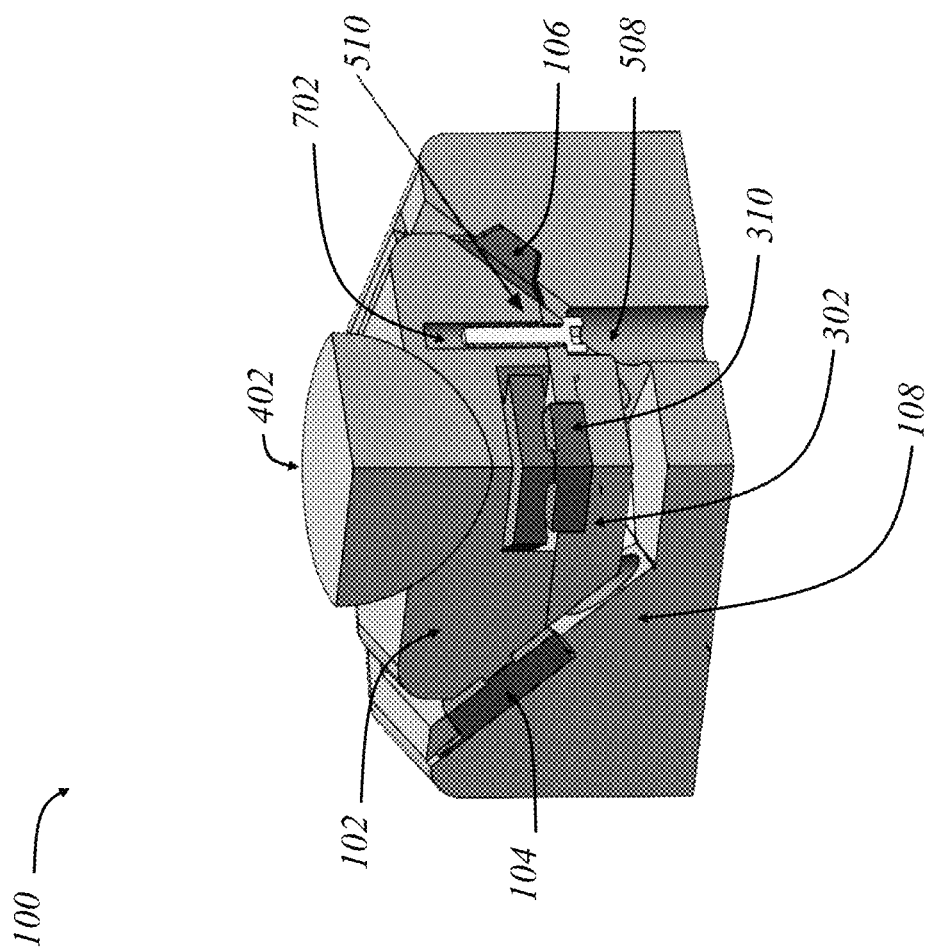
FIG. 7 is another example cross-sectional view of the joint implant device of FIG. 4, in accordance with implementations.

FIG. 6 depicts an example cross-sectional view of the implant device 100 and FIG. 7 depicts another example cross-sectional view of the implant device 100 cut along a different axis. As depicted in FIGS. 6 and 7, the first fasteners 502 and the second fasteners 510 facilitate rigidly coupling the socket housing extension 308 with the socket housing 108 and the socket extension 302 with the socket 102. As depicted in at least FIG. 7, the aperture 508 of the socket extension 302 can extend at least partially through a portion of the socket housing 108.

The socket 102 can rigidly couple with the socket extension 302 (e.g., by the second fastener 510 or by another technique including, but not limited to, threads, clasps, or other components) such that movement of the socket 102 can cause the socket extension 302 to move. The socket housing 108 can rigidly couple with the socket housing extension 308 (e.g., by the first fastener 502 or by another technique including, but not limited to, threads, clasps, or other components) such that movement of the socket housing 108 can cause the socket extension 302 to move.

For example, as described herein, if a force of the ball 402 is exerted along a portion of the socket 102 outside of a range of one or more of the direct sensors (e.g., the first sensor 104, the second sensor 106, or the third sensor 202), the force can cause the socket 102 to pivot slightly. The pivoting of the socket 102 can cause movement of the socket extension 302 relative to the socket housing extension 308. This movement can cause a compression force between one or more portions of the socket extension 302 and socket housing extension 308 such that a compression force is exerted at, on, or near the indirect sensor (e.g., the fourth sensor 310). In this manner, the implant device 100 can have at least ¾ sensor readings regardless of the force or rotation of the ball 402 when the implant device 100 includes four sensors. As described herein, the implant device 100 can include more or less sensors.

Figure 8:
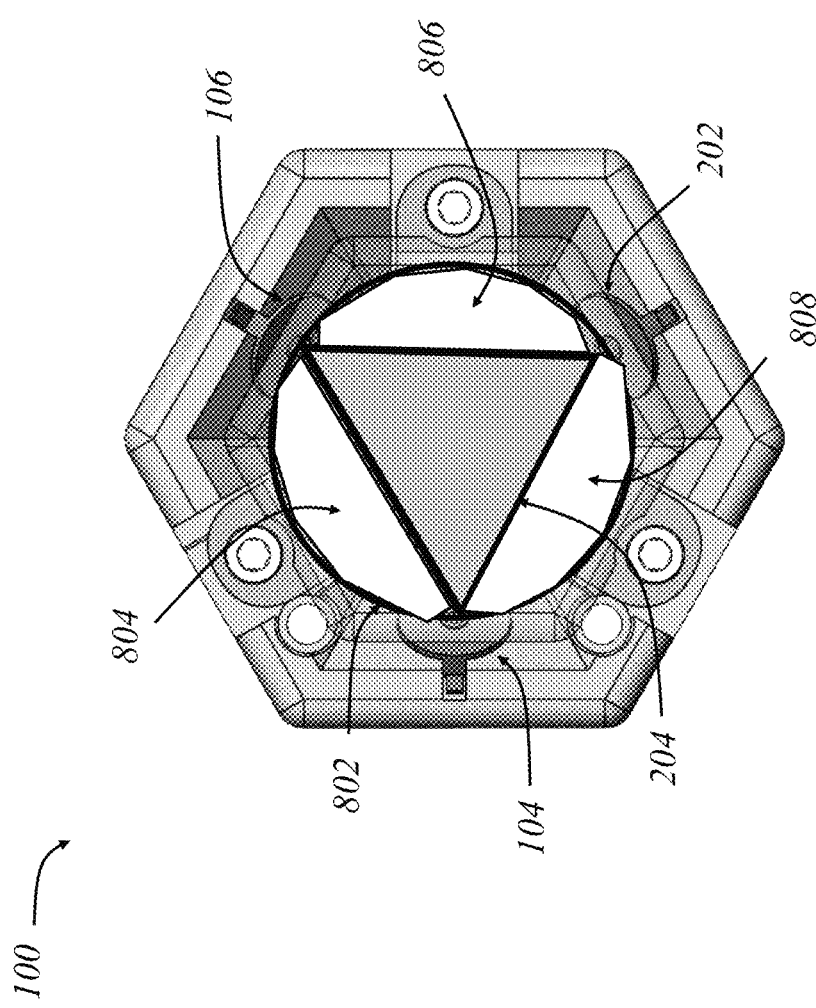
FIG. 8 is an example top schematic view of the joint implant device of FIG. 4, in accordance with implementations.

FIG. 8 depicts an example top schematic view of a portion of the implant device 100. For example, FIG. 8 depicts a schematic of the triangular area 204 of the sensors 104, 106, 202 and a circular representation 802 of an interface between the ball 402 and a surface of the socket 102. The area 204 and the representation 802 are represented as standard shapes (e.g., triangular and circular) for illustrative purposes. The area 204 and representation 802 can include other shapes (e.g., rectangular, unsymmetrical, abstract, or another shape).

The circular representation 802 can overlap the triangular area 204 at least at one point such that one or more zones are formed between the area 204 and the circular representation 802. For example, a first zone 804 can be disposed between the triangular area 204 and the circular representation 802 between the first sensor 104 and the second sensor 106. The first zone 804 can represent an area of space along the socket 102 in which a force applied by the ball 402 is outside of the third sensor 202. For example, if a force is applied within the first zone 804, the force can cause the socket 102 to pivot about the first sensor 104 or the second sensor 106 such that a compression force is no longer applied, or is too weak, at the third sensor 202. In this case, the pivoting of the socket 102 can cause a compression force between the socket extension 302 and the socket housing extension 308 such that the fourth sensor 310 is compressed, as described herein. The force can be determined based on signals between the first sensor 104, the second sensor 106, and the fourth sensor 310.

A second zone 806 can be disposed between the triangular area 204 and the circular representation 802 between the second sensor 106 and the third sensor 202. The second zone 806 can represent an area of space along the socket 102 in which a force applied by the ball 402 is outside of the first sensor 104. For example, if a force is applied within the second zone 806, the force can cause the socket 102 to pivot about the second sensor 106 or the third sensor 202 such that a compression force is no longer applied, or is too weak, at the first sensor 104. In this case, the pivoting of the socket 102 can cause a compression force between the socket extension 302 and the socket housing extension 308 such that the fourth sensor 310 is compressed, as described herein. The force can be determined based on signals between the second sensor 106, the third sensor 202, and the fourth sensor 310.

A third zone 808 can be disposed between the triangular area 204 and the circular representation 802 between the first sensor 104 and the third sensor 202. The third zone 808 can represent an area of space along the socket 102 in which a force applied by the ball 402 is outside of the second sensor 106. For example, if a force is applied within the third zone 808, the force can cause the socket 102 to pivot about the first sensor 104 or the third sensor 202 such that a compression force is no longer applied, or is too weak, at the second sensor 106. In this case, the pivoting of the socket 102 can cause a compression force between the socket extension 302 and the socket housing extension 308 such that the fourth sensor 310 is compressed, as described herein. The force can be determined based on signals between the first sensor 104, the third sensor 202, and the fourth sensor 310.

Figure 9:
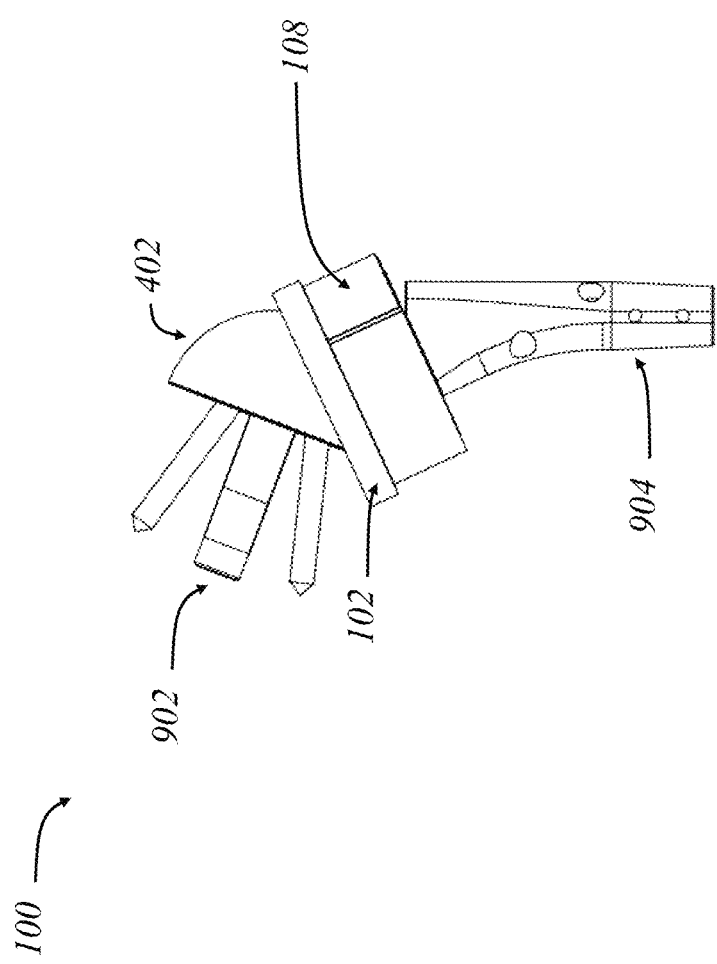
FIG. 9 is an example side view of a joint implant device, in accordance with implementations.
Figure 10:
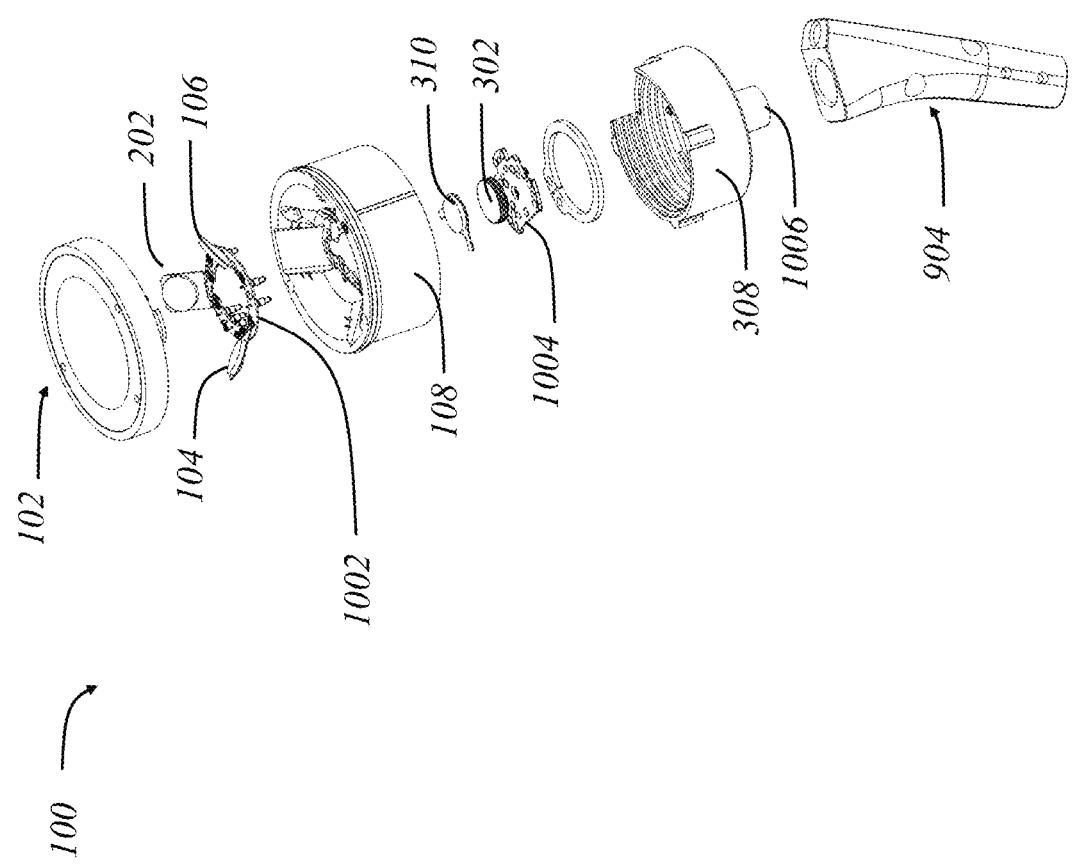
FIG. 10 is an example exploded view of the joint implant device of FIG. 9, in accordance with implementations.

FIG. 9 depicts a side view of the implant device 100 and FIG. 10 depicts an exploded view of the implant device 100. As described herein, the implant device 100 can couple with one or more joint components. For example, the ball 402 in FIG. 9 is depicted as a glenosphere having one or more first joint components 902 (e.g., extensions, protrusions, fasteners, or other components) to couple with a portion of a joint or other part of the body (e.g., a portion of the shoulder, elbow, knee, hip, or other portion of the body). The first joint component 902 can be or can couple with various other components of a joint including, but not limited to, a femoral head. The first joint components 902 can extend from or couple with a portion of a first end of the implant device 100.

The implant device 100 can include or can couple with at least one second joint component 904. For example, the socket housing extension 308 can include one or more protrusions 1006 that extends from the housing extension 308 to facilitate coupling with the second joint component 904. The second joint component 904 can extend from an opposing second end of the implant device 100. The second joint component 904 can extend from another portion of the implant device 100. The second joint component 904 can include or can be a humeral component (e.g., a stem, an extension, a protrusion, an aperture, or another component). The second joint component 904 can include or can be a pelvic component or various other joint components. The ball 402 (e.g., such as a glenosphere or femoral head) can couple with a first portion of the joint and can rotate relative to the socket 102 which can couple with a second portion of the joint to form a ball and socket joint.

As depicted in at least FIG. 10, the first sensor 104, the second sensor 106, and the third sensor 202 can be disposed beneath a surface of the socket 102 to facilitate detecting any force applied to the socket 102 (e.g., by the ball 402). For example, the first sensor 104, the second sensor 106, and the third sensor 202 can each be coupled with (e.g., connected to) a first printed circuit board 1002 (e.g., via one or more pins). The fourth sensor 310 can couple with the first printed circuit board 1002. For example, the fourth sensor 310 can couple with the first printed circuit board 1002 via one or more pogo pins. The fourth sensor 310 can couple with a second printed circuit board 1004. The first printed circuit board 1002 can communicably couple with the second printed circuit board 1004. For example, one or more signals can be transmitted between the first printed circuit board 1002 and the second printed circuit board 1004 by one or more communication channels (e.g., by one or more wires or wirelessly). For example, at least one of the first printed circuit board 1002 or the second printed circuit board 1004 can include one or more RF components.

Figure 11:
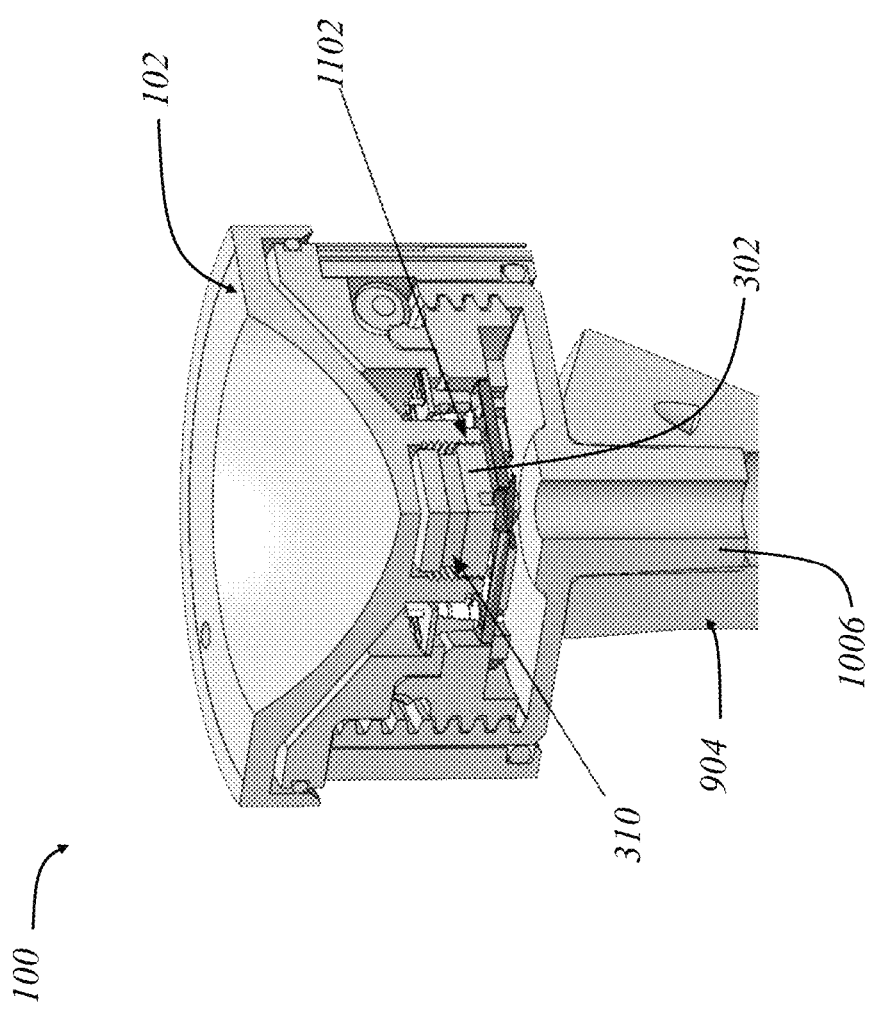
FIG. 11 is an example cross-sectional view of the joint implant device of FIG. 9, in accordance with implementations.
Figure 12:
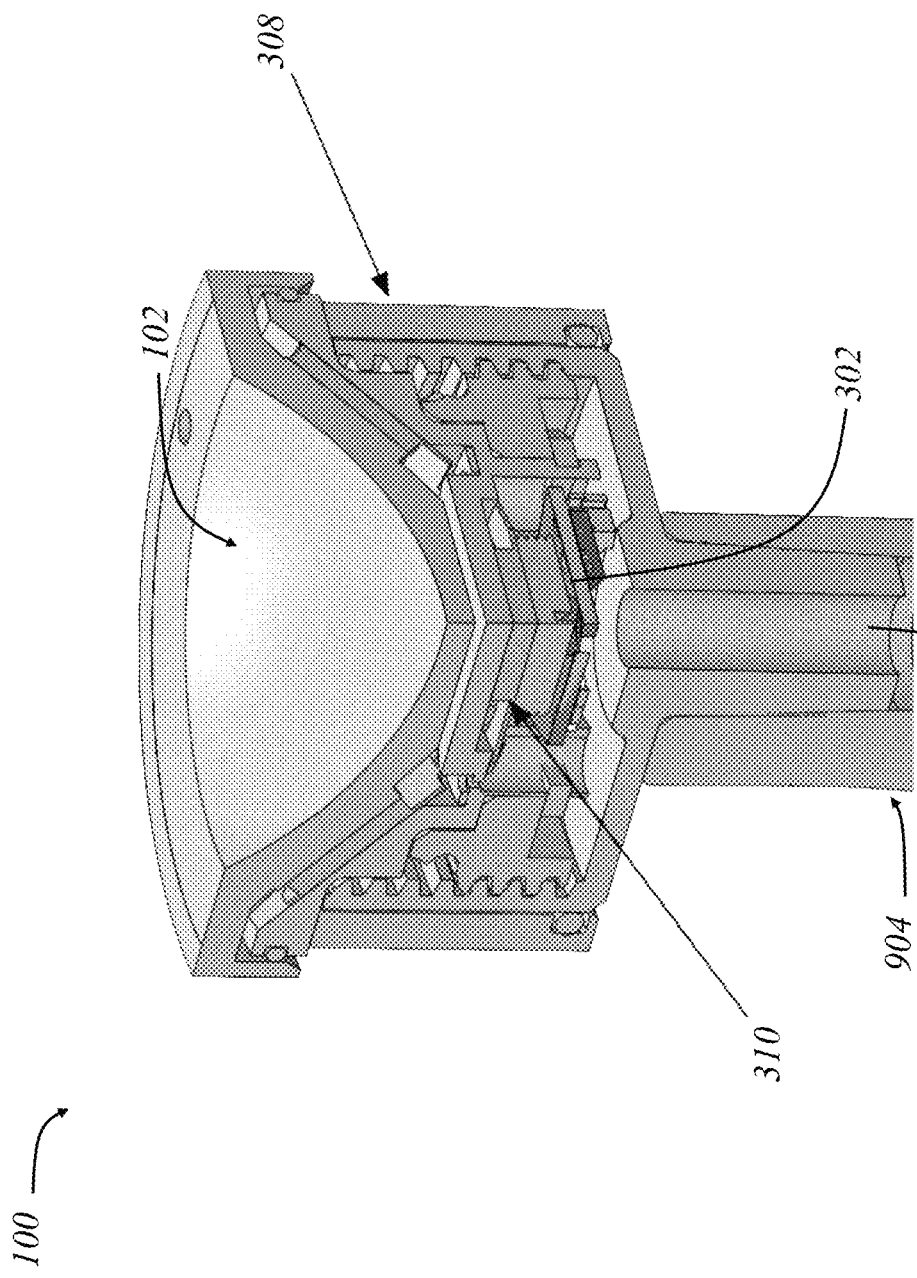
FIG. 12 is another example cross-sectional view of the joint implant device of FIG. 9, in accordance with implementations.

FIG. 11 and FIG. 12 depict example cross-sectional views of the implant device 100. As depicted in at least FIGS. 11 and 12, the implant device 100 can include at least one threaded rigid connection (e.g., one or more corresponding or opposing threads to threadably connect two components). For example, the implant device 100 can include at least one threaded rigid connection 1102 between the socket 102 and the socket extension 302 to rigidly couple the socket 102 and the socket extension 302.

The implant device 100 can include an antenna. For example, the implant device 100 can include an antenna embedded within a portion of the socket 102, the socket housing 108, or another portion of the implant device 100. For example, the antenna (e.g., a PCB antenna) can circumferentially surround one or more portions of the implant device 100 (e.g., spiral around, wrap around). The antenna can communicably couple with the one or more sensors. The antenna can communicably couple with one or more internal module or external modules to transmit signals of the sensors to or from the modules. The external module can include a patch, reinforcement, or the like to adhere to a portion of a patient's body (e.g., stick to the skin). The sensors, the antenna, the external module, and the internal module can communicably couple with one another such that signals detected by the first sensor 104, the second sensor 106, the third sensor 202, and the fourth sensor 310 can be communicated to a computing device external to the body of the patient (e.g., external to the implant device 100). For example, a user interface of a computer communicably coupled with the sensors can receive and display information from the sensors such that a user of the computer can interpret (e.g., read, see, visualize) data from the sensors.

As described herein, the first sensor 104, the second sensor 106, the third sensor 202, and the fourth sensor 310 can facilitate determining and detecting a load force applied to the socket 102. For example, the load force (e.g., a magnitude and direction) can be determined by the sum of forces measured by the first sensor 104, the second sensor 106, and the third sensor 202, plus the sum of the forces measured by the fourth sensor 310. For illustrative purposes, the first sensor 104, the second sensor 106, and the third sensor 202 can be referred to as direct sensors and the fourth sensor 310 can be referred to as an indirect sensor. The amount of direct or indirect sensors can vary. For example, the implant device 100 can include M amount of direct sensors and N amount of indirect sensors. In these circumstances, the load force can be determined by the sum of the M forces measured by the direct sensors, plus the sum of the N forces measured by the indirect sensors.

Figure 13:
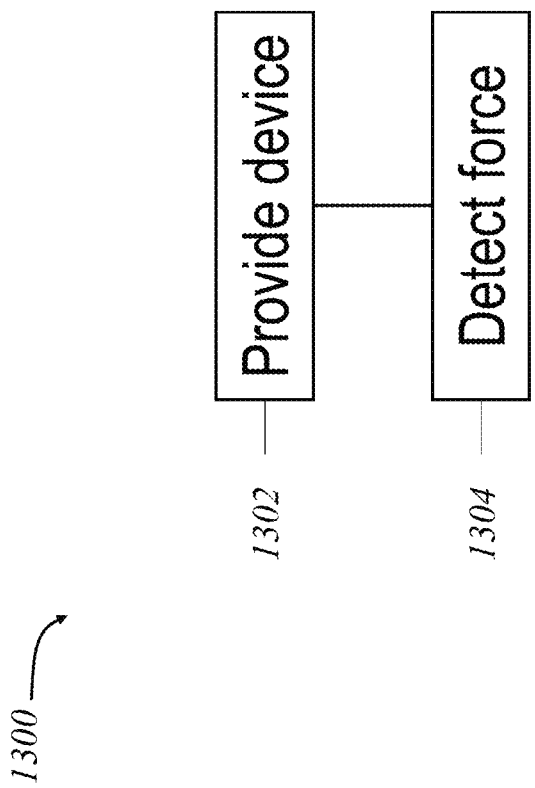
FIG. 13 is an example illustration of a method, in accordance with implementations.

FIG. 13 depicts an illustration of a method 1300. The method 1300 can include providing the joint implant device 100, as depicted in act 1302. For example, the implant device 100 can include the socket 102. The socket 102 can at least partially receive a portion of a first joint component. For example, the socket 102 can at least partially receive the ball 402 (e.g., a glenoid sphere, a femoral head, or another portion of a joint). The socket 102 can couple with the socket housing 108. The socket housing 108 can position beneath or at least partially around the socket 102 (e.g., opposite the surface that receives the ball 402) such that the socket housing 108 supports the socket 102.

The implant device 100 can include the first sensor 104, the second sensor 106, the third sensor 202, or the fourth sensor 310. The first sensor 104, the second sensor 106, and the third sensor 202 can be disposed between the socket 102 and the socket housing 108. The first sensor 104, the second sensor 106, and the third sensor 202 can be equally spaced circumferentially about a center portion of the socket 102 (e.g., about a center portion of the ball 402 when the ball 402 is received by the socket 102). The first sensor 104, the second sensor 106, and the third sensor 202 can be equally spaced to define the triangular area 204 in which the direct sensors can detect a force.

The implant device 100 can include the socket extension 302 rigidly coupled with the socket 102 and the socket housing extension 308 rigidly coupled with the socket housing 108. The fourth sensor 310 can be disposed at least partially between the socket housing extension 308 and the socket extension 302.

The method 1300 can include detecting a force between the socket 102 and the first joint component (e.g., the ball 402) by at least three of the four sensors, as depicted in act 1304. For example, as described herein, if the force is exerted at a point within the triangular area 204, the first sensor 104, the second sensor 106, and the third sensor 202 can facilitate detecting the magnitude and direction of the force. If the force is exerted at a portion outside of the triangular area 204 (e.g., within one of the first zone 804, the second zone 806, or the third zone 808), at least two of the first sensor 104, the second sensor 106, and the third sensor 202 in combination with the fourth sensor 310 can facilitate detecting the magnitude and direction of the force.

Figure 14:
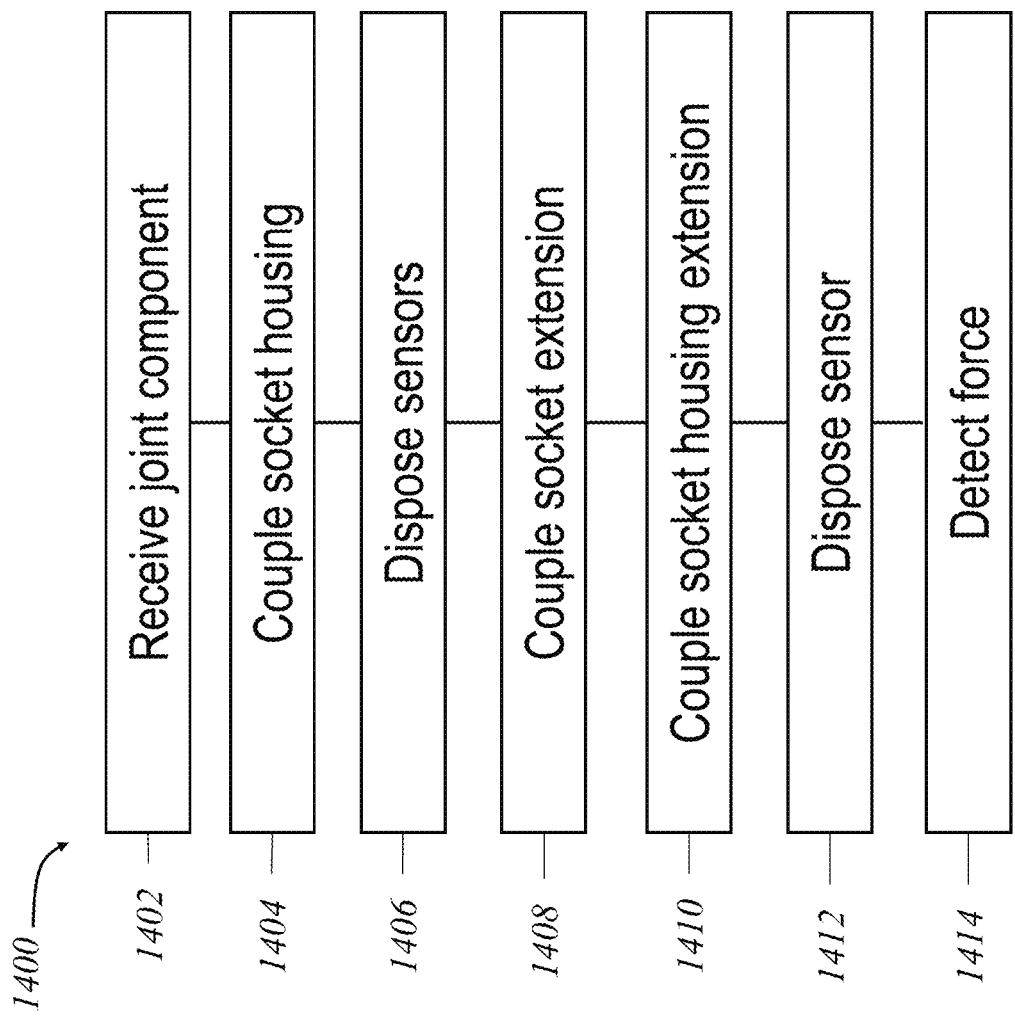
FIG. 14 is an example illustration of a method of providing a joint implant device, in accordance with implementations.

FIG. 14 depicts an illustration of a method 1400. The method 1400 can include at least partially receiving, by the socket 102, a first joint component, as depicted in act 1402. For example, the first joint component can be or can include the ball 402 (e.g., a glenosphere or a femoral head). The first joint component can be or can include one or more portions of a joint of a body that can couple with the socket 102. For example, the socket 102 can include one or more surfaces (e.g., an annular surface) that can receive a portion of the first joint component. The socket 102 can include one or more materials coupled with the annular surface to facilitate coupling with the first joint component.

The method 1400 can include coupling the socket housing 108 with the socket 102, as depicted in act 1404. For example, one or more fasteners (e.g., the second fastener 510) can facilitate coupling the socket 102 with the socket housing 108. As another example, one or more rigid threads connections can facilitate coupling the socket 102 with the socket housing 108. The socket 102 and the socket housing 108 can couple with one another in various other ways including, but not limited to, welding or adhesives.

The method 1400 can include disposing the first sensor 104, the second sensor 106, and the third sensor 202 between the socket 102 and the socket housing 108, as depicted in act 1406. For example, as described herein, the direct sensors can be disposed between a lower surface of the socket 102 and an upper surface of the socket housing 108 such that the direct sensors can detect a force applied to the socket 102 by being directly compressed by the force.

The method 1400 can include coupling the socket extension 302 with the socket 102, as depicted in act 1408. For example, the socket extension 302 can couple with the socket 102 by at least one second fastener 510 as depicted in at least FIG. 7. For example, the socket 102 can include an aperture 702 and the socket extension 302 can include a corresponding aperture 508 that can align with one another to receive a portion of the second fastener 510.

The method 1400 can include coupling the socket housing extension 308 with the socket housing 108, as depicted in act 1410. For example, the socket housing extension 308 can couple with the socket housing 108 by at least one first fastener 502 as depicted in at least FIG. 6. For example, the socket housing 108 can include an aperture 506 and the socket housing extension can include a corresponding aperture 504 that can align with one another to receive a portion of the first fastener 502.

The method 1400 can include disposing the fourth sensor 310 between the socket extension 302 and the socket housing extension 308, as depicted in act 1412. The fourth sensor 310 can be disposed such that the fourth sensor 310 can be compressed between at least a portion of the socket extension 302 and the socket housing extension 308. For example, the fourth sensor 310 can couple with the second printed circuit board 1004 which can be disposed between the socket extension 302 and the socket housing extension 308. The fourth sensor 310 can indirectly detect a force of the socket 102 by compression between the socket extension 302 and the socket housing extension 308.

The method 1400 can include detecting, by at least three of the first sensor 104, the second sensor 106, the third sensor 202, or the fourth sensor 310, a force between the socket 102 and the first joint component, as depicted in act 1414. For example, as described herein, if the force is exerted within the triangular area 204, the first sensor 104, the second sensor 106, and the third sensor 202 can detect and determine the force. If the force is exerted outside of the triangular area 204, two of the first sensor 104, the second sensor 106, and the third sensor 202 in combination with the fourth sensor 310 can detect and determine the force.

FIG. 15 depicts an illustration of a method 1500. The method 1500 can include providing the joint implant device 100, as depicted in act 1502. For example, the implant device 100 can include the socket 102. The socket 102 can at least partially receive a portion of a first joint component. For example, the socket 102 can at least partially receive the ball 402 (e.g., a glenoid sphere, a femoral head, or another portion of a joint). The socket 102 can couple with the socket housing 108. The socket housing 108 can position beneath or at least partially around the socket 102 (e.g., opposite the surface that receives the ball 402) such that the socket housing 108 supports the socket 102.

The implant device 100 can include the first sensor 104, the second sensor 106, the third sensor 202, or the fourth sensor 310. The first sensor 104, the second sensor 106, and the third sensor 202 can be disposed between the socket 102 and the socket housing 108. The first sensor 104, the second sensor 106, and the third sensor 202 can be equally spaced circumferentially about a center portion of the socket 102 (e.g., about a center portion of the ball 402 when the ball 402 is received by the socket 102). The first sensor 104, the second sensor 106, and the third sensor 202 can be equally spaced to define the triangular area 204 in which the direct sensors can detect a force.

The implant device 100 can include the socket extension 302 rigidly coupled with the socket 102 and the socket housing extension 308 rigidly coupled with the socket housing 108. The fourth sensor 310 can be disposed at least partially between the socket housing extension 308 and the socket extension 302.

The first sensor 104, the second sensor 106, and the third sensor 202 can detect and transmit signals corresponding to a load force or other physical parameter when a load force is applied within the triangular area 204. At least two of the first sensor 104, the second sensor 106, and the third sensor 202, in combination with the fourth sensor 310, can detect and transmit signals corresponding to a load force or other physical parameter when a load force is applied outside of the triangular area 204 and within range of at least two of the first sensor 104, the second sensor 106, and the third sensor 202 (e.g., within the first zone 804, the second zone 806, or the third zone 808).

The computing system(s) described herein can include clients and servers. A client and server are generally remote from each other and typically interact through a communication network. The relationship of client and server arises by virtue of computer programs running on the respective computers and having a client-server relationship to each other. In some implementations, a server transmits data (e.g., data packets) to a client device (e.g., for purposes of displaying data to or receiving user input from a user interacting with the client device). Data generated at the client device (e.g., a result of the user interaction) can be received from the client device at the server.

The separation of various system components does not require separation in all implementations, and the described program components can be included in a single hardware or software product. For example, the components described herein can be a single component, app, or program, or a logic device having one or more processing circuits, or executed by one or more processors of the data processing system(s).

Some of the description herein emphasizes the structural independence of the aspects of the system components. Other groupings or components that execute similar overall operations are understood to be within the scope of the present application. Modules or components can be implemented in hardware or as computer instructions on a non-transient computer readable storage medium, and modules can be distributed across various hardware or computer based components.

The systems described above can provide multiple ones of any or each of those components and these components can be provided on either a standalone system or on multiple instantiation in a distributed system. In addition, the systems and methods described above can be provided as one or more computer-readable programs or executable instructions embodied on or in one or more articles of manufacture. The article of manufacture can be cloud storage, a hard disk, a CD-ROM, a flash memory card, a PROM, a RAM, a ROM, or a magnetic tape. In general, the computer-readable programs can be implemented in any programming language, such as LISP, PERL, C, C++, C #, PROLOG, or in any byte code language such as JAVA. The software programs or executable instructions can be stored on or in one or more articles of manufacture as object code.

Example and non-limiting module implementation elements include sensors providing any value determined herein, sensors providing any value that is a precursor to a value determined herein, datalink or network hardware including communication chips, oscillating crystals, communication links, cables, twisted pair wiring, coaxial wiring, shielded wiring, transmitters, receivers, or transceivers, logic circuits, hard-wired logic circuits, reconfigurable logic circuits in a particular non-transient state configured according to the module specification, any actuator including at least an electrical, hydraulic, or pneumatic actuator, a solenoid, an op-amp, analog control elements (springs, filters, integrators, adders, dividers, gain elements), or digital control elements.

The subject matter and the operations described herein can be implemented in digital electronic circuitry, or in computer software, firmware, or hardware, including the structures disclosed in this specification and their structural equivalents, or in combinations of one or more of them. The subject matter described herein can be implemented as one or more computer programs, e.g., one or more circuits of computer program instructions, encoded on one or more computer storage media for execution by, or to control the operation of, data processing apparatuses. The program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. While a computer storage medium is not a propagated signal, a computer storage medium can be a source or destination of computer program instructions encoded in an artificially generated propagated signal. The computer storage medium can also be, or be included in, one or more separate components or media (e.g., multiple CDs, disks, or other storage devices include cloud storage). The operations described in this specification can be implemented as operations performed by a data processing apparatus on data stored on one or more computer-readable storage devices or received from other sources.

The terms "computing device", "component" or "data processing apparatus" or the like encompass various apparatuses, devices, and machines for processing data, including by way of example a programmable processor, a computer, a system on a chip, or multiple ones, or combinations of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, app, script, or code) can be written in any form of programming language, including compiled or interpreted languages, declarative or procedural languages, and can be deployed in any form, including as a stand-alone program or as a module, component, subroutine, object, or other unit suitable for use in a computing environment. A computer program can correspond to a file in a file system. A computer program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatuses can also be implemented as, special purpose logic circuitry, e.g., an FPGA (field programmable gate array) or an ASIC (application specific integrated circuit). Devices suitable for storing computer program instructions and data can include non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

The subject matter described herein can be implemented in a computing system that includes a back end component, e.g., as a data server, or that includes a middleware component, e.g., an application server, or that includes a front end component, e.g., a client computer having a graphical user interface or a web browser through which a user can interact with an implementation of the subject matter described in this specification, or a combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

While operations are depicted in the drawings in a particular order, such operations are not required to be performed in the particular order shown or in sequential order, and all illustrated operations are not required to be performed. Actions described herein can be performed in a different order.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one implementation are not intended to be excluded from a similar role in other implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation" or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

References to "or" may be construed as inclusive so that any terms described using "or" may indicate any of a single, more than one, and all of the described terms. References to at least one of a conjunctive list of terms may be construed as an inclusive OR to indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

Modifications of described elements and acts such as variations in sizes, dimensions, structures, shapes and proportions of the various elements, values of parameters, mounting arrangements, use of materials, colors, orientations can occur without materially departing from the teachings and advantages of the subject matter disclosed herein. For example, elements shown as integrally formed can be constructed of multiple parts or elements, the position of elements can be reversed or otherwise varied, and the nature or number of discrete elements or positions can be altered or varied. Other substitutions, modifications, changes and omissions can also be made in the design, operating conditions and arrangement of the disclosed elements and operations without departing from the scope of the present disclosure.

Systems and methods described herein may be embodied in other specific forms without departing from the characteristics thereof. For example, the joint implant device 100 can be implanted in a shoulder joint, a knee joint, an ankle joint, or a hip joint. Further relative parallel, perpendicular, vertical or other positioning or orientation descriptions include variations within +/−10% or +/−10 degrees of pure vertical, parallel or perpendicular positioning. References to "approximately," "about" "substantially" or other terms of degree include variations of +/−10% from the given measurement, unit, or range unless explicitly indicated otherwise. Coupled elements can be electrically, mechanically, or physically coupled with one another directly or with intervening elements. Scope of the systems and methods described herein is thus indicated by the appended claims, rather than the foregoing description, and changes that come within the meaning and range of equivalency of the claims are embraced therein.

What is claimed is:

1. A joint implant device, comprising:
a socket that at least partially receives a first joint component;
a socket housing coupled with the socket;
a first sensor, a second sensor, and a third sensor each coupled with the socket housing and disposed between the socket and the socket housing, at least one of the first sensor, the second sensor, or the third sensor to detect a reaction force between the socket and the socket housing;
a socket extension coupled with the socket between the socket and the socket housing;
a socket housing extension coupled with the socket housing between the socket extension and the socket;
a fourth sensor coupled with the socket extension and disposed between the socket extension and the socket housing extension, the fourth sensor to detect a reaction force between the socket extension and the socket housing extension; and
at least three of the first sensor, the second sensor, the third sensor, or the fourth sensor to detect a force between the socket and the first joint component.

2. The joint implant device of claim 1, comprising:
the first sensor, the second sensor, and the third sensor equally spaced about the socket in a circumferential direction about a center of the socket; and
the first sensor, the second sensor, and the third sensor to detect a load force exerted on the socket within a triangular area between the first sensor, the second sensor, and the third sensor.

3. The joint implant device of claim 1, comprising:
the first sensor, the second sensor, and the third sensor equally spaced about the socket in a circumferential direction about a center of the socket;
the first sensor, the second sensor, and the third sensor to detect a load force exerted on the socket within a triangular area between the first sensor, the second sensor, and the third sensor; and
at least two of the first sensor, the second sensor, or the third sensor, and the fourth sensor to detect a load force exerted on the socket outside of the triangular area between the first sensor, the second sensor, and the third sensor.

4. The joint implant device of claim 1, comprising:
the socket extension rigidly coupled with the socket by at least one first fastener;
the socket housing extension rigidly coupled with the socket housing by at least one second fastener; and
pivoting of the socket causes the socket extension to compress a portion of the socket housing extension.

5. The joint implant device of claim 1, comprising:
the socket extension rigidly coupled with the socket by at least one first threaded joint;
the socket housing extension rigidly coupled with the socket housing by at least one second threaded joint; and
pivoting of the socket causes the socket extension to compress a portion of the socket housing extension.

6. The joint implant device of claim 1, comprising:
the first sensor, the second sensor, and the third sensor coupled with a first printed circuit board;
the fourth sensor coupled with a second printed circuit board; and
at least a portion of the first printed circuit board communicably coupled with at least a portion of the second printed circuit board.

7. The joint implant device of claim 1, comprising:
at least one end of the socket housing to couple with a second joint component;
the first joint component is at least one of a glenoid sphere or a femoral head; and
the second joint component is at least one of a humeral component or a pelvic component.

8. The joint implant device of claim 1, comprising:
the at least three of the first sensor, the second sensor, the third sensor, or the fourth sensor to detect a magnitude and a direction of the force between the socket and the first joint component.

9. The joint implant device of claim 1, comprising:
at least one of the first sensor, the second sensor, the third sensor, or the fourth sensor includes a compression sensor.

10. A method, comprising:
providing a joint implant device, the joint implant device including:
   a socket that at least partially receives a first joint component;
   a socket housing coupled with the socket;
   a first sensor, a second sensor, and a third sensor each coupled with the socket housing and disposed between the socket and the socket housing, at least one of the first sensor, the second sensor, or the third sensor to detect a reaction force between the socket and the socket housing;
   a socket extension coupled with the socket between the socket and the socket housing;
   a socket housing extension coupled with the socket housing between the socket extension and the socket; and
   a fourth sensor coupled with the socket extension and disposed between the socket extension and the socket housing extension, the fourth sensor to detect a reaction force between the socket extension and the socket housing extension.

11. The method of claim 10, comprising:
the first sensor, the second sensor, and the third sensor equally spaced about the socket in a circumferential direction about a center of the socket; and
detecting, by the first sensor, the second sensor, and the third sensor, a load force exerted on the socket within a triangular area between the first sensor, the second sensor, and the third sensor.

12. The method of claim 10, comprising:
the first sensor, the second sensor, and the third sensor equally spaced about the socket in a circumferential direction about a center of the socket;
the first sensor, the second sensor, and the third sensor to detect a load force exerted on the socket within a triangular area between the first sensor, the second sensor, and the third sensor; and
detecting, by at least two of the first sensor, the second sensor, or the third sensor, and the fourth sensor, a load force exerted on the socket outside of the triangular area between the first sensor, the second sensor, and the third sensor.

13. The method of claim 10, comprising:
the socket extension rigidly coupled with the socket by at least one first fastener;
the socket housing extension rigidly coupled with the socket housing by at least one second fastener; and
compressing, by the socket extension, a portion of the socket housing extension responsive to pivoting of the socket.

14. The method of claim 10, comprising:
the socket extension rigidly coupled with the socket by at least one first threaded joint;
the socket housing extension rigidly coupled with the socket housing by at least one second threaded joint; and
compressing, by the socket extension, a portion of the socket housing extension responsive to pivoting of the socket.

15. The method of claim 10, comprising:
the first sensor, the second sensor, and the third sensor coupled with a first printed circuit board;
the fourth sensor coupled with a second printed circuit board; and
at least a portion of the first printed circuit board communicably coupled with at least a portion of the second printed circuit board.

16. The method of claim 10, comprising:
at least one end of the socket housing to couple with a second joint component;
the first joint component is at least one of a glenoid sphere or a femoral head; and
the second joint component is at least one of a humeral component or a pelvic component.

17. The method of claim 10, comprising:
at least three of the first sensor, the second sensor, the third sensor, or the fourth sensor to detect a magnitude and a direction of a force between the socket and the first joint component.

18. The method of claim 10, comprising:
at least one of the first sensor, the second sensor, the third sensor, or the fourth sensor includes a compression sensor.

19. The method of claim 10, comprising:
detecting, by at least three of the first sensor, the second sensor, the third sensor, or the fourth sensor, a force between the socket and the first joint component.

20. A method of providing a joint implant device, comprising:
at least partially receiving, by a socket, a first joint component;
coupling a socket housing with the socket;
disposing a first sensor, a second sensor, and a third sensor between the socket and the socket housing, at least one of the first sensor, the second sensor, or the third sensor to detect a reaction force between the socket and the socket housing;
coupling a socket extension with the socket between the socket and the socket housing;
coupling a socket housing extension with the socket housing between the socket extension and the socket;
disposing a fourth sensor between the socket extension and the socket housing extension, the fourth sensor to detect a reaction force between the socket extension and the socket housing extension; and
detecting, by at least three of the first sensor, the second sensor, the third sensor, or the fourth sensor, a force between the socket and the first joint component.

* * * * *